(12) United States Patent  
Battula

(10) Patent No.: US 9,113,979 B2
(45) Date of Patent: Aug. 25, 2015

(54) DENTAL IMPLANT DEVICES, KITS, AND METHODS

(75) Inventor: Suneel Ranga Sai Battula, San Diego, CA (US)

(73) Assignee: Zimmer Dental, Inc., Carlsbad, CA (US)

(*) Notice: Subject to any disclaimer, the term of this patent is extended or adjusted under 35 U.S.C. 154(b) by 0 days.

(21) Appl. No.: 13/544,731

(22) Filed: Jul. 9, 2012

(65) Prior Publication Data

US 2013/0011814 A1 Jan. 10, 2013

Related U.S. Application Data

(60) Provisional application No. 61/505,177, filed on Jul. 7, 2011.

(51) Int. Cl.
*A61C 8/00* (2006.01)
*A61C 8/02* (2006.01)
*A61C 19/06* (2006.01)

(52) U.S. Cl.
CPC ............. *A61C 8/0068* (2013.01); *A61C 8/0006* (2013.01); *A61C 8/0018* (2013.01); *A61C 19/06* (2013.01)

(58) Field of Classification Search
CPC ... A61C 8/0068; A61C 8/0006; A61C 8/0012
USPC ......... 433/172–176, 201.1; 623/17.17–17.19, 623/17.11–23.63; 606/60, 62–68, 300–331
See application file for complete search history.

(56) References Cited

U.S. PATENT DOCUMENTS

| 4,252,525 | A  | * | 2/1981 | Child .......................... 433/173 |
|---|---|---|---|---|
| 5,282,861 | A  |   | 2/1994 | Kaplan |
| 7,112,063 | B2 | * | 9/2006 | Bulard et al. ................. 433/174 |
| 2004/0053196 | A1 | * | 3/2004 | Mayer et al. .................. 433/173 |
| 2006/0078847 | A1 | * | 4/2006 | Kwan ........................... 433/174 |
| 2006/0084034 | A1 | * | 4/2006 | Hochman ...................... 433/173 |
| 2008/0206716 | A1 | * | 8/2008 | Asgary ....................... 433/228.1 |
| 2008/0241793 | A1 | * | 10/2008 | Collins et al. ................. 433/174 |
| 2009/0317768 | A1 | * | 12/2009 | Mayer et al. ................ 433/201.1 |
| 2010/0196841 | A1 | * | 8/2010 | Nahlieli et al. ................. 433/29 |

* cited by examiner

*Primary Examiner* — Edward Moran
(74) *Attorney, Agent, or Firm* — Schwegman Lundberg & Woessner, P.A.

(57) ABSTRACT

Dental implant devices, kits, and methods for implantation or use in a bone cavity, are disclosed. A dental implant can include a body portion, extending from a proximal end to a distal end along a longitudinal axis, including a central bore extending from the proximal end to a termination point, located proximal of the distal end. The dental implant can further include and one or more channels extending between the central bore and an exterior surface of the body portion. A kit can include a set of different sized dental implants, a set of slugs including a resorbable material, and optionally, an injection tool. A method can include inserting the dental implant into a bone cavity, introducing a resorbable material into the central bore of the body portion, and permitting the resorbable material to flow from the central bore, through the one or more channels, and into the bone cavity.

19 Claims, 7 Drawing Sheets

DENTAL IMPLANT DEVICES, KITS, AND METHODS

CLAIM OF PRIORITY

This patent document claims the benefit of priority, under 35 U.S.C. Section 119(e), to U.S. Provisional Patent Application Ser. No. 61/505,177, entitled "USE OF RESORBABLE MATERIAL TO STABILIZE DENTAL IMPLANT," filed on Jul. 7, 2011, which is hereby incorporated by reference herein in its entirety.

TECHNICAL FIELD

This disclosure generally relates to implants and, more particularly, to dental implants.

BACKGROUND

A dental implant can be used in an oral treatment procedure to restore appearance or function of a removed tooth. A dental implant can mimic a root of a natural tooth that is replaced. A surgeon can replace the natural tooth with a prosthetic tooth that is mounted on a proximal portion of an abutment, which in turn, is attached to the dental implant on a distal portion. During surgery, the surgeon can insert the dental implant into a dental bone cavity.

OVERVIEW

Dental implants can mimic the root of a tooth that is intended to be replaced. Dental implants can include a cylindrical exterior surface that can be press fit into a dental bone cavity, such as by inserting the dental implant into an osteotomy created by a surgeon or inserting the dental implant into a cavity resulting from an extraction of the tooth. Optionally, the exterior surface of a dental implant can include one or more threads to urge the implant into the bone cavity and create retaining threads in the adjacent bone. The one or more threads can also lead to bone compaction around the dental implant, which can provide initial implant stability and help shield the dental bone from load bearing activity during the healing process or osseointegration.

The success of inserting a dental implant can be dependent on the quantity and quality of the dental bone that the implant is inserted into. In some instances, the surgeon can determine bone at an implant site is unsuitable for receiving the dental implant. Unsuitable dental bone can include soft bone or bone associated with patients suffering from osteo-disorders or dental conditions (e.g., conditions associated with smoking or diabetes) that provide insufficient stability (e.g., resistance/holding strength) to the dental implant during and after surgery. A bone grafting procedure can be performed to augment dental bone, particularly otherwise unsuitable bone, at the implant site. A bone grafting process can require a period of 12-16 weeks for bone healing/growth before the dental implant can be inserted at the intended location.

The present inventor has recognized, among other things, a need to increase the initial stability of a dental implant during and immediately after surgery and to increase the suitability of dental bone that may otherwise be deemed unsuitable for receipt of the dental implant. It is believed that an introduction of a resorbable material into a bone cavity can increase the initial stability of the dental implant by forming a stabilizing layer between the dental bone surrounding the bone cavity and the dental implant. In some examples, the dental implant can include a center bore and one or more channels extending between the center bore and an exterior surface of the implant. The resorbable material can be introduced into the center bore and allowed to distribute to the dental bone cavity through the one or more channels.

Occasionally, a dental implant that has been inserted within a dental bone cavity can fail (e.g., due to a fracture or infection). In such an instance, a surgeon may need to perform an additional surgery to remove and replace the failed dental implant. Depending on the length of time the failed implant had been implanted, the failed dental implant may have started to osseointegrate, in which case the surgeon has to create a dental bone cavity that is larger than the failed implant. Depending on size and space limitations of a patient's oral cavity, it may not be desirable to use a larger dental implant to replace the failed dental implant.

The present inventor has further recognized that the introduction of a resorbable material into a dental bone cavity to form a stabilizing layer between dental bone and a dental bone implant can be used to stabilize dental implants having a smaller size than dental bone cavities in which they are inserted. For instance, threads of a dental implant may not come into contact with surrounding dental bone during implantation. The resorbable material can fill the surrounding area between the dental implant threads and the dental bone to provide initial stability until in-growth around and into the dental implant can occur.

To better illustrate the dental implant devices, kits, and methods disclosed herein, a non-limiting list of examples is provided here:

In Example 1, a dental implant comprises a body portion, extending from a proximal end to a distal end along a longitudinal axis, including a central bore extending from the proximal end to a termination point, located proximal of the distal end, and one or more channels extending between the central bore and an exterior surface of the body portion.

In Example 2, the dental implant of Example 1 is optionally configured such that the central bore is in fluid communication with the exterior surface.

In Example 3, the dental implant of any one or any combination of Example 1 or 2 is optionally configured such that at least one channel, of the one or more channels, is oriented at an angle relative to a plane that is orthogonal to the longitudinal axis of the body portion.

In Example 4, the dental implant of any one or any combination of Examples 1-3 is optionally configured such that the one or more channels include a diameter within a range of about 0.25 millimeters to about 3.0 millimeters, inclusive.

In Example 5, the dental implant of any one or any combination of Examples 1-4 is optionally configured such a surface of the central bore includes a threaded portion, configured to engage with a threaded connector.

In Example 6, the dental implant of any one or any combination of Examples 1-5 is optionally configured such that the exterior surface of the body portion includes a threaded portion defined by a continuous thread or a plurality of distinct threads.

In Example 7, the dental implant of Examples 6 is optionally configured such that each of the one or more channels include an opening, at the exterior surface of the body portion, the openings positioned between the continuous thread or the plurality of distinct threads of the threaded portion.

In Example 8, the dental implant of any one or any combination of Examples 1-7 is optionally configured such that the exterior surface of the body portion includes a non-threaded portion.

In Example 9, the dental implant of Example 8 is optionally configured such that each of the one or more channels include an opening, at the exterior surface of the body portion, the openings positioned along the non-threaded portion.

In Example 10, the dental implant of Example 1 is optionally configured such that he body portion includes a threaded portion, defined by a continuous thread or a plurality of distinct threads, and a non-threaded portion, and wherein a plurality of the one or more channels include an opening, at the exterior surface of the body portion, the openings positioned along the non-threaded portion.

In Example 11, the dental implant of Example 10 is optionally configured such that the body portion includes a core portion, defined by an outer diameter less than an outer diameter of an adjacent body portion, and wherein at least one channel, of the one or more channels, extends between the central bore and an exterior surface of the core portion.

In Example 12, the dental implant of Example 11 is optionally configured to further comprise a porous sleeve positioned about the exterior surface of the core portion.

In Example 13, a dental implant kit comprises a set of different sized dental implants, at least one of the dental implants, comprising a body portion, extending from a proximal end to a distal end along a longitudinal axis, including a central bore extending from the proximal end to a termination point, located proximal of the distal end, and one or more channels extending between the central bore and an exterior surface of the body portion. The kit further comprises a set of slugs including a resorbable material, and an injection tool, configured to heat the resorbable material to a temperature greater than its crystallization temperature.

In Example 14, the dental implant kit of Example 13 is optionally configured such that at least two slugs, of the set of slugs, include different compositions from each other.

In Example 15, the dental implant kit of any one or any combination of Examples 15 or 16 is optionally configured to further comprise a surgical tool configured to exert a force, along the longitudinal axis in an apical direction, from within the central bore.

In Example 16, a method comprises inserting a dental implant, including a body portion, having a central bore and an exterior surface, and one or more channels extending between the central bore and the exterior surface, into a dental bone cavity. The method includes introducing a resorbable material into the central bore, and permitting the resorbable material to flow from the central bore, through the one or more channels, and into the dental bone cavity, including forming a stabilizing layer between the exterior surface of the body portion and the dental bone cavity.

In Example 17, the method of Example 16 is optionally configured to further comprise heating the resorbable material to an insertion temperature that is greater than its crystallization temperature resorbable material to an insertion temperature.

In Example 18, the method of any one or any combination of Examples 16 or 17 is optionally configured such that heating the resorbable material to the insertion temperature includes generating a material temperature greater than about 42 degrees Celsius.

In Example 19, the method of any one or any combination of Examples 16-18 is optionally configured such that permitting the resorbable material to flow from the central bore, through the one or more channels, and into the dental bone cavity includes inserting a surgical tool into the central bore and applying a force along a bore axis in an apical direction.

In Example 20, the method of any one or any combination of Examples 16-19 is optionally configured such that introducing the resorbable material into the central bore includes introducing a resorbable polymer and at least one of an allograft material, an autograft material, and a xenograft material into the central bore. into the central bore.

In Example 21, the method of any one or any combination of Examples 16-20 is optionally configured such that introducing the resorbable material into the central bore includes introducing a resorbable polymer, selected from polylactic acid, polyglycolic acid, polycaprolactone, a bone morphogenetic protein, a human growth hormone, an anti-inflammatory, an anti-biotic, and a radio-opaque substance, and at least one of an allograft material, an autograft material, and a xenograft material including demineralized bone matrix.

In Example 22, the dental implant device, kit, or method of any one or any combination of Examples 1-21 is optionally configured such that all elements or options recited are available to use or select from.

These and other examples and features of the present dental implant devices, kits, and methods will be set forth in the following Detailed Description. This Overview is intended to provide non-limiting examples of the present subject matter and is not intended to provide an exclusive or exhaustive explanation. The Detailed Description below is included to provide further information about the present dental implant devices, kits, and methods.

BRIEF DESCRIPTION OF THE DRAWINGS

In the drawings, like numerals can be used to describe similar elements throughout the several views. The drawings illustrate generally, by way of example, but not by way of limitation, various embodiments discussed in the present patent document.

DETAILED DESCRIPTION

It can be desirable to increase an initial stability of a dental implant, particularly in patients having soft bone or patients suffering from osteo-disorders or dental conditions. The present dental implant devices, kits, and methods provide for stabilization of a dental implant within a dental bone cavity. A dental implant can include a center bore and one or more channels extending between the center bore and an exterior surface of the implant. A resorbable material can be introduced into the center bore and allowed to distribute to the dental bone cavity through the one or more channels. The resorbable material can provide stability to the dental implant by forming a stabilizing layer between dental bone and the dental implant.

Figure 1:
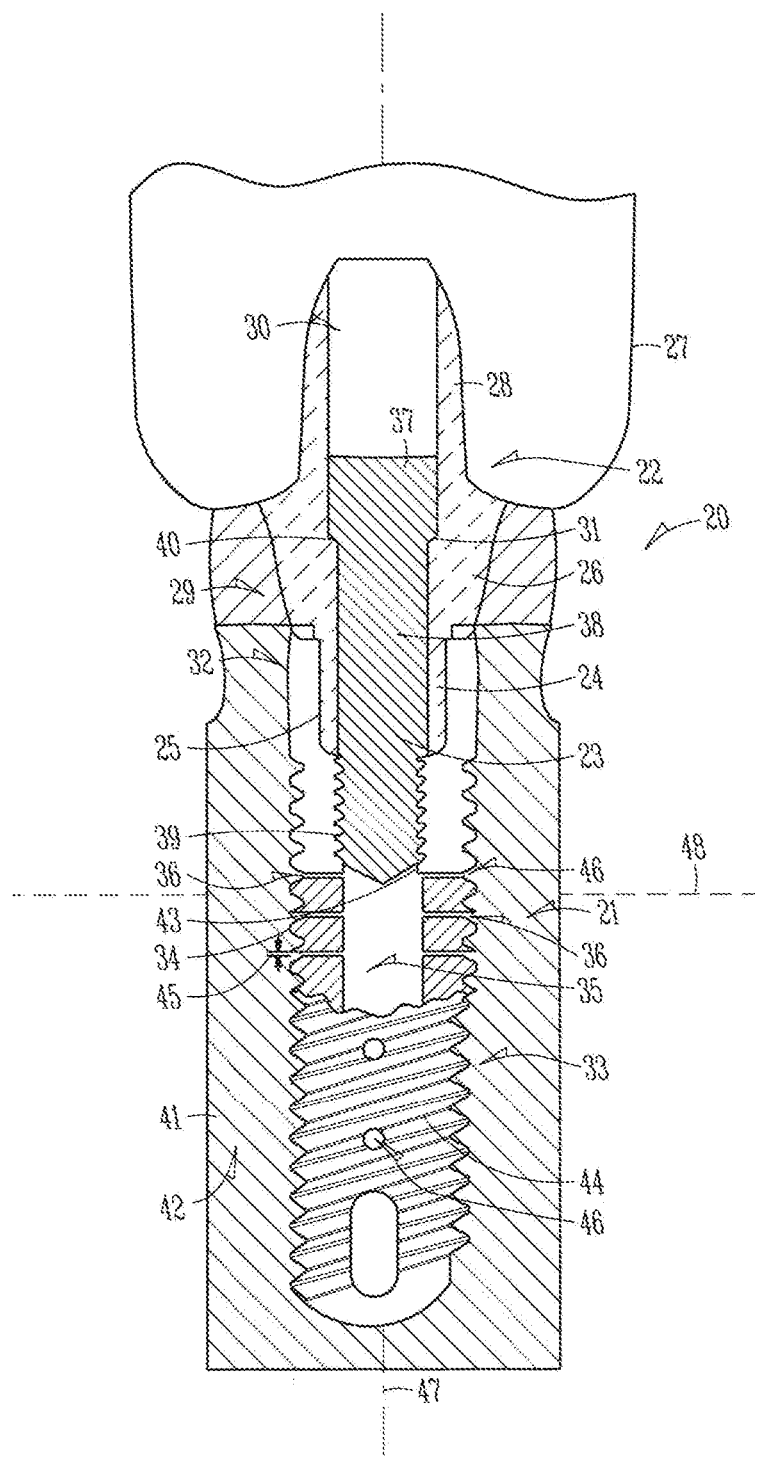
FIG. 1 illustrates a cross-sectional view of a dental prosthetic apparatus, including a dental implant inserted into a dental bone, as constructed in accordance with at least one embodiment.

FIG. 1 illustrates an example of a dental prosthetic apparatus 20 including a dental implant 21, an abutment 22, and a connector 23 interconnecting the dental implant 21 and the abutment 22. The dental implant 21, the abutment 22, and the connector 23 can provide an anchor for a prosthetic tooth 27 (e.g., a crown) at an edentulous site in a patient's dentition, where a natural tooth has been lost, damaged, or removed. The abutment 22 can include a base 24 configured to mate with the dental implant 21. The base 24 can be frictionally retained by a similarly-shaped recess 25 formed in the dental implant 21. In an example, the base 24 can have a polygonal exterior surface including a plurality of flat surfaces. The recess 25 in the dental implant 21 can include a polygonal inner surface including a plurality of generally flat surfaces configured to mate with the base 24 of the abutment 22.

The abutment 22 can include a transgingival portion 26 configured to extend through soft gingival tissue, and a supragingival portion 28 configured to extend beyond the transgingival portion 26 and attach to a prosthetic tooth 27 (e.g., a crown). The abutment 22 can include a body 29 having a center bore 30. The center bore 30 can include a step 31 for abutting engagement by the connector 23, thereby securing the abutment 22 to the dental implant 21.

The abutment 22 can be manufactured from a variety of biocompatible materials, such as aluminum oxide, zirconium oxide, commercially pure titanium, titanium alloy, ceramic, or gold. In addition, portions of the abutment 22 (e.g., the transgingival portion 26) can be anodized or coated with a nitride material, such as titanium nitride or another colorizing agent to provide a desired color or other surface property. Titanium nitride coating can create a golden, more aesthetically pleasing color on the surface of the abutment as compared with untreated titanium. Portions of the abutment 22 can also be treated, coated, or roughened to promote soft tissue adhesion or growth in the areas on or adjacent to the treated surfaces.

The connector 23 can secure the abutment 22 to the dental implant 21. The connector 23 can include a head 37 including an engagement surface 40 configured to abut step 31 of the abutment 22. The connector 23 can include a shank 38 extending from the head 37 to a threaded tail 39.

Configuration options for the abutment are numerous. For example, the abutment 22 can be attached to the dental implant 21 by various means and can depend on the type of implant 21 used by the surgeon. For example, the abutment 22 may be attached to the dental implant 21 by, for example, conical connections, internal or external connections, and non-friction fitting attachment mechanisms. The dimensions and shapes of the trangingival portion 26 and the supragingival portion 28 of the abutment 22 can be varied to match the needs of each individual patient. Factors, such as the amount of space available and the orientation of the implant, can influence the surgeon's decision on the abutment to select when performing a tooth restoration on a patient.

The abutment 22 can be mounted to the dental implant 21 by inserting the base 24 into the recess 25 and then inserting the connector 23 into the coronal end of the center bore 30. The connector 23 can be inserted through the center bore 30 of the abutment 22, with the threaded tail 39 being threaded into an internally threaded region 43 of a central bore 35 of the dental implant 21. The tail 39 can be threaded until the head 37 of the connector 23 abuts the step 31 of the center bore 30 of the abutment 22.

As discussed above, the dental implant 21 can be fitted into a dental cavity 42 formed in a patient's dental bone 41. The dental implant 21 can include a collar portion 32 and a body portion 33. The collar portion 32 can be the portion of the dental implant 21 forming the recess 25 in which the base 24 of the abutment is inserted. The collar portion 32 can be threaded, partially threaded, or non-threaded, the latter of which is illustrated in FIG. 1.

The dental implant 21 can include a longitudinally extending body portion 33, having a proximal end and a distal end, adapted to be implanted into the dental cavity 42 formed in the dental bone 41 of a patient. The dental cavity 42 can be formed according to known surgical techniques, for example, by a surgeon drilling into a patient's jaw bone at an edentulous site. The body portion 33 of the dental implant 21 can include an exterior surface 34 for interacting with bone tissue, thereby securing the dental implant 21 to the dental bone 41 through osseointegration or other biological or mechanical interactions. The body portion 33 can be made of a biocompatible metal, for example, titanium.

Figure 2:
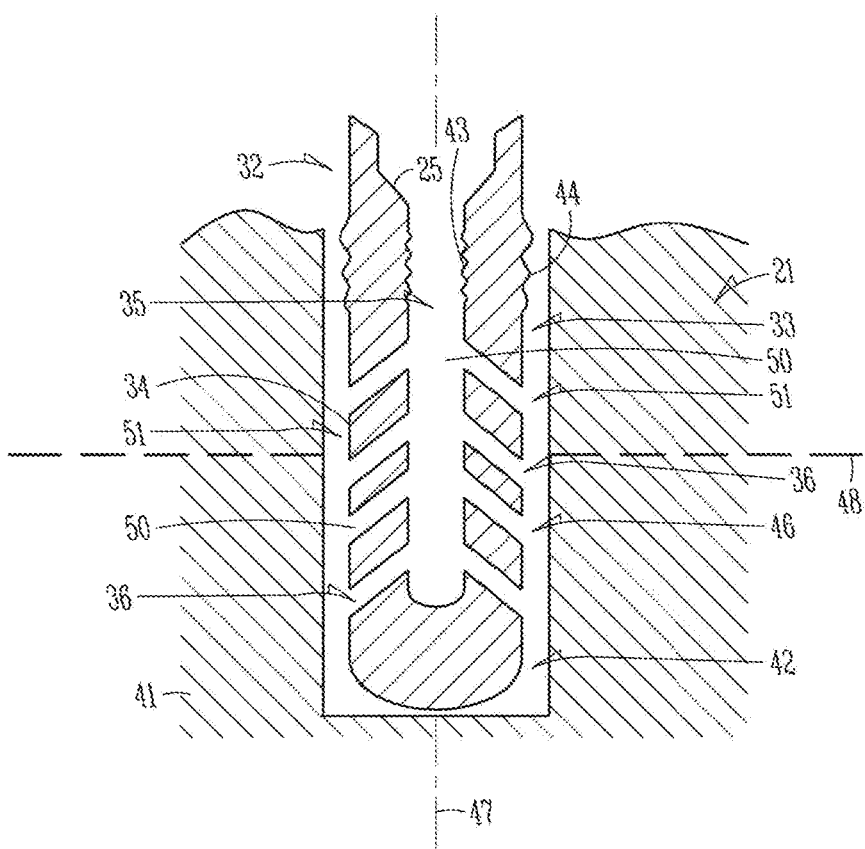
FIG. 2 illustrates a cross-sectional view of a dental implant, inserted into a dental bone cavity, and a stabilizing layer of resorbable material disposed between the dental bone and dental implant, as constructed in accordance with at least one embodiment.

The body portion 33 can be cylindrical, partially cylindrical, or tapered in shape. The body portion 33 can define a central bore 35 extending to a termination point, such as is illustrated in FIG. 2. The central bore 35 can include a threaded portion 43 configured to interact with the threaded tail 23 of the connector 23 to secure the abutment 22 to the dental implant 21.

The body portion 33 can further include one or more channels 36 extending between the central bore 35 and the exterior surface 34. The central bore 35 can be in fluid communication with the exterior surface 34 by way of the one or more channels 36. Each channel 36 can include an opening 46 at the exterior surface 34, which can be sized and shaped to allow resorbable material to flow from the central bore 35 to the dental cavity 42. Once in the dental cavity 42, the resorbable material can form a stabilizing layer between the dental implant 21 and the dental bone 41.

In some examples, as illustrated in FIG. 1, the channels 36 can be oriented orthogonal to a longitudinal axis 47 of the dental implant 21. In some examples, the channels 36 can be oriented at an angle relative to a plane or axis 43 that is orthogonal to the longitudinal axis 47, as illustrated in FIG. 2. In some examples, the channels 36 can be parallel to the other channels 36. In other examples, one or more channels 36 are not parallel to the other channels 36.

The channels 36 can include a variety of shapes and sizes. For example, the channels 36 can be formed as circles, ovals, triangles, squares, rectangles, hexagons, heptagons, octagons, or combinations thereof. The channels 36 can have a uniform width or diameter 45. In some examples, the width or diameter 45 can vary. In some examples, each of the one or more channels 36 can have the same width or diameter 45. In some examples, the one or more channels 36 can have different widths or diameters 45 with respect to each other. In some examples, the width or diameter of the channels 36 can range from about 0.25 millimeters (mm) to about 3.0 mm.

The number and location of the channels 36 can also vary. A factor in determining the number and location of the channels 36 can depend on the quality of the patient's dental bone. For example, if dental bone positioned coronal to the prosthetic tooth is more damaged than dental bone positioned apically from the prosthetic tooth, it can be desirable to provide additional stabilization along the portion of the dental bone that is more damaged. In that instance, a dental implant with one or more channels positioned towards the coronal end of the body portion 33 can be used. As a result, when resorbable material is introduced into the central bore 35 and allowed to flow through the channels 36 into the dental cavity 42, the resorbable material will be introduced and form a stabilizing layer between the dental implant 21 and the dental bone 41 that is more damaged.

The exterior surface 34 of the dental implant 21 can be threaded, partially threaded, or non-threaded. The exterior surface 34 can be cylindrical or partially cylindrical. As illustrated in FIG. 1, the exterior surface 34 can be cylindrical and include threads 44 along a length of the body portion 33. The channels 36 can be positioned along the length of the body portion 33. In some examples, the threads 44 and the channels 36 can overlap. That is, the openings 46 of the channels 36 can be positioned between continuous or discrete threads 44, partially on the threads 44, or over the threads 44.

FIG. 2 illustrates a cross-sectional view of a dental implant 21 inserted into a dental bone cavity 42 of a dental bone 41. A stabilizing layer of resorbable material 50 is disposed between the dental bone 41 and the dental implant 21. The dental implant 21 can include a body portion 33 that is partially threaded and implanted into the dental cavity 42. The body portion 33 can include continuous or discrete threads 44 positioned on a portion of its exterior surface 34. The body portion 33 can define a central bore 35 extending from a coronal or proximal end to a termination point 49.

As illustrated in FIG. 2, the channels 36 can be oriented at an angle relative to a plane or axis 48 that is orthogonal to a longitudinal axis 47 of the dental implant 21. The resorbable material 50 has been introduced into the central bore 35 and has flowed from the central bore 35, through the channels 26, and into the dental cavity 42 to form a stabilizing layer 51 between the dental implant 21 and the dental bone 41.

In some examples, the resorbable material 50 can be a blend of a resorbable polymer and at least one of an allograft material, an autograft material, and a xenograft material. The term "resorbable" is used herein to refer to a material that maintains its structural integrity during an initial period of time, but is capable of being disintegrated and absorbed by a living body over time. For example, resorbable polymers suitable for use with the present dental implants 21 can include, but are not limited to, polylactic acid, polyglycolic acid, polyhydroxybutyrate, and polyhydroxyvalerate, and copolymers therof, polycaprolactone, polyanhydrides, polyorthoesters, and other biodegradable polymers. Moreover, allograft materials suitable for use with the present dental implants 21 can include, but are not limited to, demineralized bone matrix (DBM), such as DBM sold by Zimmer Dental under the trade name Puros®, bone morphogenetic protein (BMP), human growth hormone (HGH), other regenerative materials derived from human body, or mixtures and blends thereof.

In addition to the resorbable polymer and allograft material, the resorbable material can include other optional ingredients. In an example, the resorbable material can further include an anti-inflammatory medication to expedite healing of the surgically created dental cavity or an antibiotic medication to prevent infections of the surgically created dental cavity. In an example, the resorbable material can further include a radio-opaque substance, such as barium sulphate, so that the resorbable material can be readily locatable by X-ray or other imaging means.

The resorbable material 50 can be delivered to the dental bone cavity 42 in a semi-solid or liquid state to facilitate the formation of the stabilizing layer 51 disposed between the dental bone 41 and the dental implant 21. Upon curing, the stabilizing layer 51 of the resorbable material 50 can provide high initial stability to the dental implant 21 and dental bone 41 interface, and can act to resist tensile and compressive forces or bending and twisting generated by the chewing motion of jaw bones.

In addition to providing stability to the dental implant 21, the resorbable material 50 can also act as a medium for in-growth of dental bone 42 around and into the dental implant 21. For example, the cured resorbable material 50 can include a stiffness less than the dental implant 21, but greater than that of the dental bone 41. In such an example, the cured resorbable material 50 can provide a buffer that can lead to improved osseointegration and increased dental bone 42 growth around the dental implant 21, as compared to an inserted dental implant 21 without the resorbable material 50.

Figure 3:
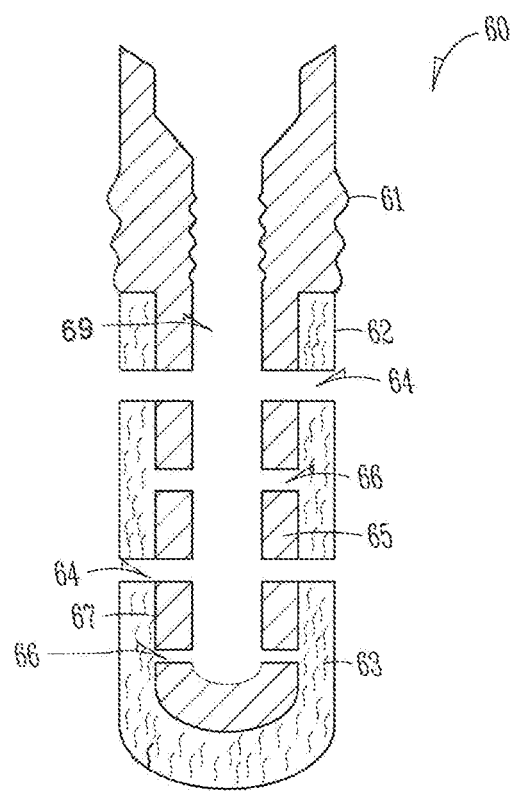
FIG. 3 illustrates a cross-sectional view of a dental implant including a porous sleeve, as constructed in accordance with at least one embodiment.

FIG. 3 illustrates a cross-sectional view of a dental implant 60 including a porous sleeve 63. The dental implant 60 can include continuous or discrete threads 61 along a portion of its exterior surface 62. To facilitate osseointegration, a non-threaded portion of the exterior surface 62 can include a porous biomaterial useful as a bone substitute or cell and tissue receptive material. Additionally, the non-threaded portion of the exterior surface 62 can be provided with a porous and osteo-inductive coating, such as hydroxylapatite.

Highly porous biomaterials can be called highly biocompatible materials. Highly biocompatible materials can include porous metallic structures such as porous tantalum, porous titanium, porous cobalt chrome, or porous zirconia dioxide, as well as polymeric scaffolds, or porous sections of the aforementioned materials incorporating bone morphogenic proteins, platelet rich plasma, allografts, xenografts, autografts, or probiotic bacteria.

In an example, the porous sleeve 63 can be made from a highly porous biomaterial. An example of such a material is produced using Trabecular Metal™ technology, which is generally available from Zimmer, Inc., of Warsaw, Ind. Trabecular Metal™ is a trademark of Zimmer, Inc. Such a material can be formed from a reticulated vitreous carbon foam substrate that is infiltrated and coated with a biocompatible metal, such as tantalum, etc., by a chemical vapor deposition ("CVD") process. An example of the CVD process is disclosed in U.S. Pat. No. 5,282,861, the disclosure of which is incorporated herein by reference in its entirety. Other metals, such as niobium, or alloys including tantalum and niobium can also be used.

The porous sleeve 63 can be positioned over a core portion 65 of the dental implant 60. The core portion 65 can extend apically from the threaded portion 61 of the dental implant 60.

As illustrated in FIG. 3, the dental implant 60 can include one or more channels 64 that extend from the central bore 69, through the core portion 65 and the porous sleeve 63, to the exterior surface 62. In this way, the central bore 69 can be in direct fluid communication with the exterior surface 62. Additionally, the dental implant 60 can include one or more internal channels 66 that extend from the central bore 69 to an exterior surface 67 of the core portion 65, but which do not extend through the porous sleeve 63. The channels 64 can allow resorbable material to flow from the central bore 69 to a dental cavity and form a stabilizing layer between the dental implant 60 and the dental bone. The internal channels 66, which do not extend to the exterior surface 62 of the dental implant 60, can allow the resorbable material to flow from the central bore 69 and into pores of the porous sleeve 63, thereby providing additional initial mechanical strength and stability to the porous sleeve 63. In an example, the resorbable material that flows through the internal channels 66 can infiltrate one or more pores of the porous sleeve 63 to enhance mechanical strength of the porous sleeve 63 and to act as a medium for in-growth of dental bone around and into the dental implant 63.

Figure 4:
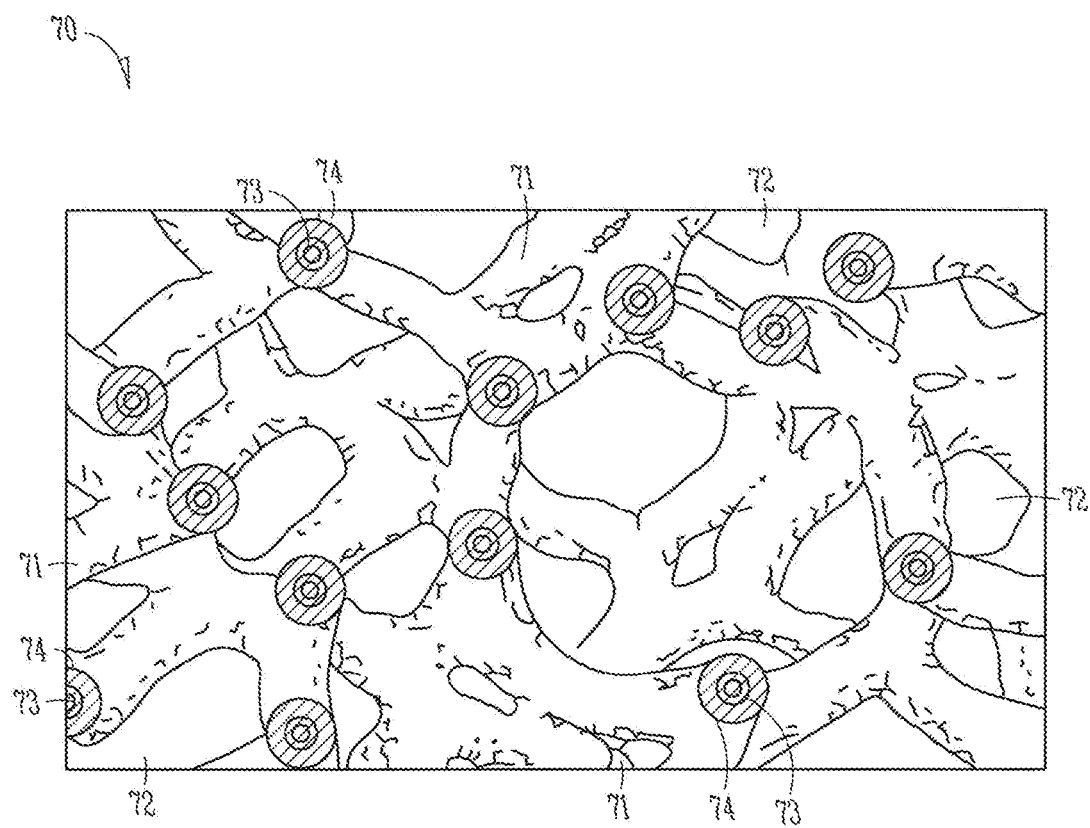
FIG. 4 illustrates a porous material that can form the porous sleeve of FIG. 3, as constructed in accordance with at least one embodiment.

FIG. 4 illustrates a porous tantalum structure 70 that can be used to form the porous sleeve 63 in FIG. 3. The porous tantalum structure 70 can include a large plurality of ligaments 71 defining open spaces 72 therebetween, with each ligament 71 generally including a carbon core 73 covered by a thin film of tantalum metal 74. The open spaces 72 between the ligaments 71 can form a matrix of continuous channels having no dead ends, such that growth of cancellous bone through the porous tantalum structure 70 is uninhibited. The porous tantalum structure 70 can include up to 75%-85% or more void space therein resulting in a lightweight, porous structure. In various examples, the porous tantalum structure 70 is substantially uniform and consistent in composition, and closely resembles the structure of natural cancellous bone, thereby providing a matrix into which cancellous bone can grow to anchor the dental implant 60 into the surrounding bone of a patient's jaw.

The porous tantalum structure 70 can be made in a variety of densities in order to selectively tailor the structure for particular applications. As discussed in the above-incorporated U.S. Pat. No. 5,282,861, the porous tantalum structure 70 can be fabricated to a desired porosity and pore size, and can be matched with the surrounding natural bone in order to provide an improved matrix for bone in-growth and mineralization.

FIGS. 5a-5d illustrate additional configurations for the example dental implants illustrated in FIGS. 1-3. Specifically, FIGS. 5a-5d illustrate the relative locations of one or more channels and threaded portions.

Figures 5A, 5B:
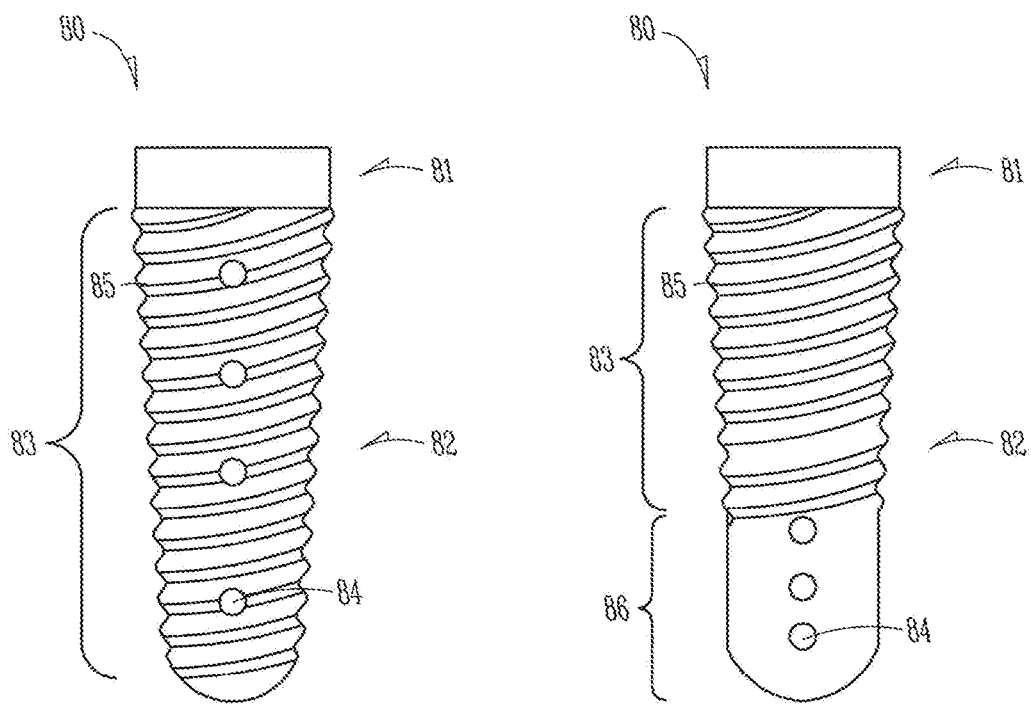
FIG. 5a illustrates an additional configuration configurations for the example dental implants illustrated in FIGS. 1-3, as constructed in accordance with at least one embodiment.
FIG. 5b illustrates an additional configuration for the example dental implants illustrated in FIGS. 1-3, as constructed in accordance with at least one embodiment.

In the example of FIG. 5a, a dental implant 80 can include a collar portion 81 and a body portion 82. The body portion 82 can include a threaded portion 83 extending along its length. The dental implant 80 can include one or more channels 84 extending along the length of the body portion 82. The channels 84 can overlap with threads 85 of the threaded portion 83.

In the example of FIG. 5b, a dental implant 80 can include a threaded portion 83 and a non-threaded portion 86, each of which can extend along a portion of a length of a body portion 82. One or more channels 84 can extend along the length of the non-threaded body portion 82. The threaded portion 83 can be positioned coronal with respect to the channels 84 and the non-threaded portion 86. Stated differently, the channels 84 can be spaced from threads 85 of the threaded portion 83. The non-threaded portion 86 can optionally include a porous sleeve, as described above with respect to FIG. 3.

Figure 5C:
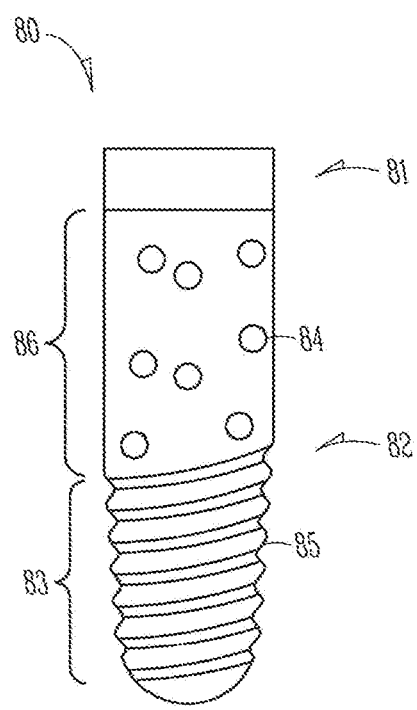
FIG. 5c illustrates an additional configuration for the example dental implants illustrated in FIGS. 1-3, as constructed in accordance with at least one embodiment.

In the example of FIG. 5C, a dental implant 80 can include a threaded portion 83 and a non-threaded portion 86, each of which can extend along a portion of a length of a body portion 82. One or more channels 84 can extend along the length of the non-threaded portion 82. The threaded portion 83 can be positioned apically with respect to the channels 84 and the non-threaded portion 86. Stated differently, the channels 84 can be spaced from threads 85 of the threaded portion 83. The non-threaded portion 86 can optionally include a porous sleeve, as described above with respect to FIG. 3.

Figure 5D:
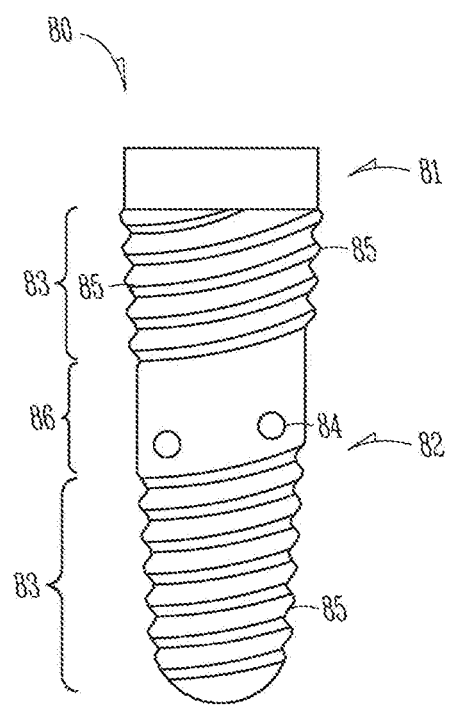
FIG. 5d illustrates an additional configuration for the example dental implants illustrated in FIGS. 1-3, as constructed in accordance with at least one embodiment.

In the example of FIG. 5d, a dental implant 80 can include a plurality of threaded portions 83 and a non-threaded portion 86, each of which can extend along a portion of a length of a body portion 82. One or more channels 84 can extend along the length of the non-threaded portion 82. A threaded portion 83 can be positioned apically and coronally with respect to the channels 84 and the non-threaded portion 86. While FIG. 5d illustrates two threaded portions 83 and one non-threaded portion 86 including channels 84, the dental implant 80 can include additional alternating threaded portions 83 and non-threaded portions 86 including channels 84. Additionally, the channels 84 can be positioned along the length of the threaded portion 83, as well as the non-threaded portion 86, in examples where the threaded portion 83 and the non-threaded portion 86 alternate along the length of the body portion 82. The non-threaded portion 86 can optionally include a porous sleeve, as described above with respect to FIG. 3.

A set of different sized dental implants can be provided in a kit to allow a surgeon to select an appropriately-sized dental implant for insertion. The different sized dental implants can comprise a body portion, extending from a proximal end to a distal end along a longitudinal axis, including a central bore extending from the proximal end to a termination point proximal of the distal end. The dental implant can further comprise one or more channels extending between the central bore and an exterior surface of the body portion. A set of slugs or tubes including a resorbable material can be provided in the kit to allow for a desired composition to be introduced into the dental cavity. Two or more of the resorbable material slugs or tubes can include a different composition. Optionally, an injection tool can be included in the dental implant set to heat the resorbable material to a temperature greater than its crystallization temperature. In an example, the dental implant kit can include a surgical tool configured to exert a force, along the longitudinal axis in an apical direction, from within the central bore. This exertion of force can assist the resorbable material to flow from the central bore to the dental bone cavity.

Figure 6:
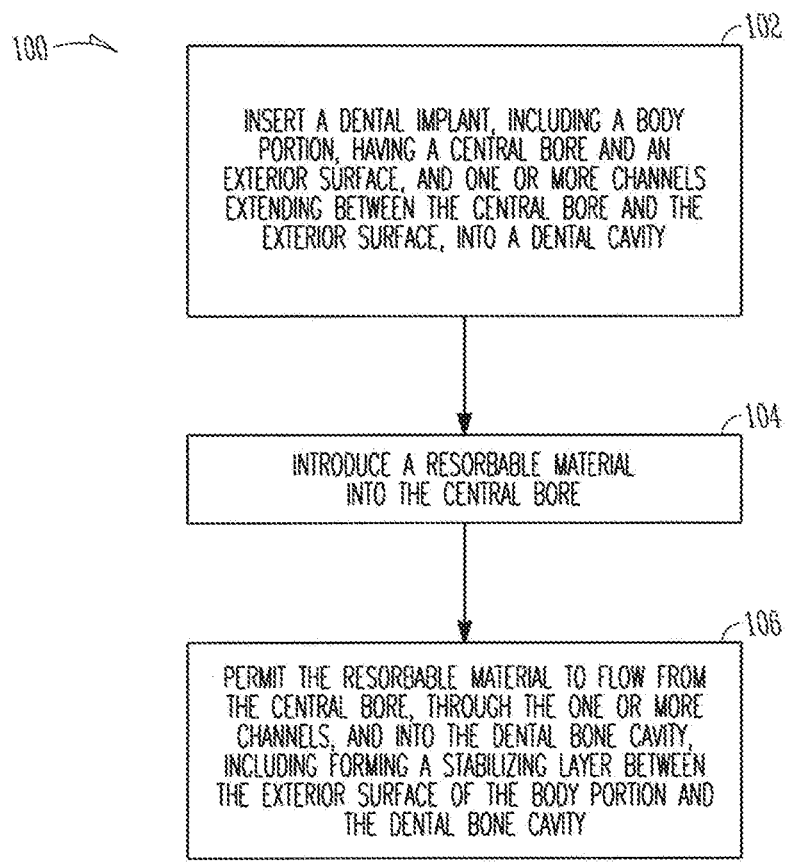
FIG. 6 illustrates a method of using a resorbable material to stabilize a dental implant, as constructed in accordance with at least one embodiment.

FIG. 6 illustrates a method 100 of using a resorbable material to stabilize a dental implant. At 102, the method 100 can include inserting a dental implant into a dental bone cavity. The dental implant can comprise a body portion having a central bore, extending from a coronal end to a termination point within the body portion, and a plurality of channels extending between the central bore and an exterior surface of the body portion. The dental implant can be inserted using any one of numerous techniques known to those skilled in the art, such as through self-tapping or press-fitting.

At 104, method 100 can include introducing a resorbable material into the central bore of the dental implant. In an example, the resorbable material can be introduced into the central bore through injection. The method 100 can further include heating the resorbable material to an insertion temperature, where the insertion temperature is greater than a crystallization temperature of the resorbable material. In an example, the resorbable material can be introduced into the central bore via an injection gun having a nozzle that melts the resorbable material and maintains it above its crystallizing temperature. In some examples, the crystallizing temperature can be equal to or greater than about 42 degrees Celsius. In various examples, the crystallizing temperature is above a temperature of the dental bone cavity such that the resorbable material can crystallize (e.g., cure) to form the stabilizing layer between the dental bone and the dental implant. The resorbable material can be packaged as slugs or tubes, each having a distinct shape or composition. The resorbable material slugs or tubes can be loaded into the injection gun, which can heat the resorbable material to the insertion temperature.

At 106, the method 100 can include permitting the resorbable material to flow from the central bore, through the one or more channels, and into the dental bone cavity, where the resorbable material forms a stabilizing layer disposed between the dental bone and the dental implant. In one example, the insertion gun can heat the resorbable material to a temperature such that the restorable material can freely flow from the central bore to the dental cavity. In other examples, a surgeon can use a surgical tool to apply a force along the longitudinal axis, in an apical direction, to force the resorbable material to flow from the central bore and through the one or more channels. The method 100 can further include allowing the resorbable material to cure (e.g., recrystalize) and form the stabilizing layer between the dental bone and the dental implant to form the stabilizing layer.

In this way, the method 100 can provide initial stability for the dental implant by mechanical, biological, or chemical interactions between the dental bone, the stabilizing layer of resorbable material, and the dental implant. As discussed herein, during osseointegration, the resorbable material can also facilitate bone growth from the dental bone, through the stabilizing layer, and to the dental implant.

In another example, the dental implant and the resorbable material may be introduced to the dental cavity simultaneously. In an example, the dental implant may be pre-packaged with the resorbable material. The dental implant can be formed to have the resorbable material positioned on the exterior surface. In an example, the resorbable material can be formed on the exterior of the dental implant, the resorbable material having a thickness within a range of about 0.5 mm to about 5 mm, inclusive. The dental implant having the resorbable material on the exterior surface can be used to provide initial stability for a dental implant that has a diameter smaller than a diameter of the dental cavity that the dental implant is to be inserted. In an example, a method can include heating the resorabable material to a temperature greater than its crystallization temperature and transferred into a mold. The mold can be cylindrical, partially cylindrical, tapered, or have other shapes. The method can include inserting the dental implant into the mold. The method can further include allowing the mold having the resorabable material and the dental implant to cool to a temperature less than the crystallization temperature of the resorbable material. Thus, the resorbable material recrystallizes and can form the dental implant having the resorabable material on the exterior surface.

A set of different sized dental implants having different thicknesses of the resorbable material formed on the exterior surface of the dental implants can be provided in a kit to allow a surgeon to select an appropriately-sized dental implant for insertion. Since the dental implants of the kit can have different thicknesses of the resorbable material formed on the exterior surface, the surgeon can select the appropriately sized dental implant regardless of the size of the dental cavity, since the resorbable material can provide initial stabilization of the dental implant.

In yet another example, the resorbable material may be introduced into the dental bone cavity prior to inserting the dental implant. In one example, once the dental cavity has been created, the surgeon can introduce a suitable amount of the resorbable material into the dental bone cavity by an injection gun, puttying, or by utilizing a surgical tool. The dental implant can be inserted into the dental bone cavity subsequent to the introduction of the resorbable material, thereby forming the stabilizing layer between the dental implant and the dental bone. Since the resorbable material can be introduced prior to inserting the dental implant, the dental implant may or may not include the central bore and one or more channels.

The above Detailed Description includes references to the accompanying drawings, which form a part of the Detailed Description. The drawings show, by way of illustration, specific embodiments in which the present dental implant devices, kits, and methods can be practiced. These embodiments are also referred to herein as "examples." While certain examples are illustrated and described with respect to a dental implant including a two-piece structure, where a separate abutment is secured to the dental implant, it is to be appreciated that the present disclosure is equally applicable to one-piece (also referred to as "uni-body") dental implant structures, where the abutment is formed integrally with the dental implant.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "coronal" and "coronally" are intended to refer to the portion of a dental implant or component that is distal to a patient's jaw bone, in the direction of a tooth or prosthetic crown, after the component has been installed in the patient. In this document, "apical" and "apically" are intended to refer to the portion of a dental implant or component that is proximal to the patient's jaw bone, or in the direction of the apex of the tooth root, after the component has been installed in the patient.

In the appended claims, the terms "including" and "in which" are used as the plain-English equivalents of the respective terms "comprising" and "wherein." The terms "including" and "comprising" are open-ended, that is, a device, kit, or method that includes elements in addition to those listed after such a term in a claim are still deemed to fall within the scope of that claim.

The Abstract is provided to allow the reader to quickly ascertain the nature of the technical disclosure. It is submitted with the understanding that it will not be used to interpret or limit the scope or meaning of the claims.

What is claimed is:

1. A dental implant, comprising:
   a body portion, extending from a proximal end to a distal end along a longitudinal axis, including a collar portion, an external threaded portion, and a core portion extending apically from the external threaded portion, the core portion having an outer diameter less than an outer diameter of the collar portion and an outer diameter of the external threaded portion, the body portion defining a central bore extending from the proximal end to a termination point within the core portion, located proximal of the distal end, wherein the proximal end is configured to receive a dental prosthesis, a porous sleeve coupled to an exterior surface of the core portion,
one or more internal channels extending between the central bore, through the core portion, and to the exterior surface of the core portion, the internal channels terminating at the exterior surface of the core portion, the internal channels structured to facilitate flow of a resorbable material from the central bore and into one or more pores of the porous sleeve to provide stability to the porous sleeve; and
one or more external channels extending between the central bore, through the core portion and the porous sleeve, and to an exterior surface of the porous sleeve, the external channels spaced apart from the externally threaded portion of the body portion to facilitate flow of the resorbable material to form a stabilizing layer between the exterior surface of the porous sleeve and a dental bone cavity.

2. The dental implant of claim 1, wherein the central bore is in fluid communication with the exterior surface of the porous sleeve.

3. The dental implant of claim 1, wherein at least one channel, of the one or more internal channels and the one or more external channels, is oriented at an angle relative to a plane that is orthogonal to the longitudinal axis of the body portion.

4. The dental implant of claim 1, wherein at least one channel, of the one or more internal channels and the one or more external channels, include a diameter within a range of about 0.25 millimeters to about 3.0 millimeters, inclusive.

5. The dental implant of claim 1, wherein a surface of the central bore includes a threaded portion, configured to engage with a threaded connector.

6. The dental implant of claim 1, wherein the external threaded portion is positioned between the collar portion and the core portion, the external threaded portion defined by a continuous thread or a plurality of distinct threads.

7. The dental implant of claim 6, wherein each of the one or more internal channels include a first opening, at the exterior surface of the core portion, and wherein each of the one or more external channels include a second opening, at the exterior surface of the porous sleeve.

8. The dental implant of claim 1, wherein an exterior surface of the collar portion includes a non-threaded portion.

9. A dental implant system, comprising:
a set of different sized dental implants, at least one of the dental implants, comprising:
a body portion, extending from a proximal end to a distal end along a longitudinal axis, including a collar portion, an external threaded portion, and a core portion extending apically from the collar portion, the core portion having an outer diameter less than an outer diameter of the collar portion and an outer diameter of the external threaded portion, the body portion defining a central bore extending from the proximal end to a termination point within the core portion, located proximal of the distal end, wherein the proximal end is configured to receive a dental prosthesis,
a porous sleeve coupled to an exterior surface of the core portion, one or more internal channels extending between the central bore, through the core portion, and to the exterior surface of the core portion, the internal channels terminating at the exterior surface of the core portion, and
one or more external channels extending between the central bore, through the core portion and the porous sleeve, and to an exterior surface of the porous sleeve;
a set of slugs including a resorbable material; and
an injection tool, configured to heat the resorbable material to a temperature greater than its crystallization temperature, wherein the one or more internal channels are configured to provide the resorbable material into pores of the porous sleeve to provide stability to the porous sleeve and the one or more external channels are spaced apart from the external threaded portion of the body portion and configured to provide the resorbable material to a dental cavity of a patient to provide a stabilizing layer between the exterior surface of the porous sleeve and the dental bone cavity.

10. The dental implant system of claim 9, wherein at least two slugs, of the set of slugs, include different compositions from each other.

11. The dental implant system of claim 9, further comprising a surgical tool configured to exert a force, along the longitudinal axis in an apical direction, from within the central bore.

12. A method, comprising:
inserting a dental implant into a dental bone cavity, the dental implant including:
a body portion, extending from a proximal end to a distal end along a longitudinal axis, the body portion including:
a collar portion,
an external threaded portion, and
a core portion extending apically from the external threaded portion, the core portion having an outer diameter less than an outer diameter of the collar portion and an outer diameter of the threaded portion, the body portion including a central bore extending from the proximal end to a termination point within the core portion, located proximal of the distal end, wherein the proximal end is configured to receive a dental prosthesis;
a porous sleeve coupled to an exterior surface of the core portion;
one or more internal channels extending between the central bore, through the core portion, and to the exterior surface of the core portion, the one or more internal channels terminating at the exterior surface of the core portion; and
one or more external channels extending between the central bore, through the core portion and the porous sleeve, and to an exterior surface of the porous sleeve;
introducing a resorbable material into the central bore;
causing the resorbable material to flow from the central bore, through the one or more internal channels, and into one or more pores of the porous sleeve to provide stability to the porous sleeve;
causing the resorbable material to flow from the central bore, through the one or more external channels, and into the dental bone cavity; and
forming a stabilizing layer between an exterior surface of the porous sleeve and the dental bone cavity.

13. The method of claim 12, further comprising heating the resorbable material to an insertion temperature that is greater than its crystallization temperature.

14. The method of claim 13, wherein heating the resorbable material to the insertion temperature includes generating a material temperature greater than about 42 degrees Celsius.

15. The method of claim 12, wherein causing the resorbable material to flow from the central bore, through the one or more internal channels, and into the one or more pores of the porous sleeve and causing the resorbable material to flow from the central bore, through the one or more external channels, and into the dental bone cavity include inserting a surgical tool into the central bore and applying a force along a bore axis in an apical direction.

16. The method of claim 12, wherein introducing the resorbable material into the central bore includes introducing a resorbable polymer and at least one of an allograft material, an autograft material, and a xenograft material into the central bore.

17. The method of claim 12, wherein introducing the resorbable material into the central bore includes introducing a resorbable polymer, selected from polylactic acid, polyglycolic acid, polycaprolactone, a bone morphogenetic protein, a human growth hormone, an anti-inflammatory, an anti-biotic, and a radio-opaque substance, the resorbable polymer including at least one of an allograft material, an autograft material, and a xenograft material including demineralized bone matrix.

18. The dental implant of claim 1, wherein the external threaded portion defines a shoulder.

19. The dental implant of claim 18, wherein a surface of the porous sleeve contacts the shoulder.

\* \* \* \* \*